United States Patent [19]

Akiyama

[11] Patent Number: 5,326,786
[45] Date of Patent: Jul. 5, 1994

[54] 5,6,7,9-TETRAHYDRO-1,2,3-TRIMETHOXY-9-OXOBENZO[ALPHA]HEPTALENE DERIVATIVE AND PHARMACEUTICAL USE

[75] Inventor: Kiyoshi Akiyama, Komatsu, Japan

[73] Assignee: Ohgen Research Laboratories Ltd., Ishikawa, Japan

[21] Appl. No.: 51,297

[22] Filed: Apr. 23, 1993

[30] Foreign Application Priority Data

Dec. 28, 1992 [JP] Japan ................................. 4-358821

[51] Int. Cl.$^5$ ...................... A61K 31/13; C07C 225/20
[52] U.S. Cl. ................................. 514/467; 514/510;
514/662; 549/451; 560/107; 560/251; 560/252;
564/427
[58] Field of Search ........................ 560/107, 291, 292;
564/427; 514/510, 467, 662; 549/451

[56] References Cited

FOREIGN PATENT DOCUMENTS 493064 7/1992 European Pat. Off. .

OTHER PUBLICATIONS van Temelen et al.,"The Synthesis of Colchicine", Tetrahedron, 1961, vol. 14, pp. 8-34, Pergamon Press.
Leiter et al., "Damage Induced in Sarcoma 37 with Chemical Agents. IV. Derivatives of Colchiceinamide¹", Journal of the National cancer-Institute, 13, pp. 731-739 (1952).
Davis, "Microbial Transformations of N-Methylcolchiceinamide", Antimicrobial Agents and Chemotherapy, Mar. 1981, vol. 19, No. 3, pp. 465-469.
Hartwell et al., "N-Substituted Colchicainamides", J. Am. Chem. Soc., vol. 74 pp. 3180-3181 (1952).

Primary Examiner—Richard L. Raymond
Attorney, Agent, or Firm—Wenderoth, Lind & Ponack

[57] ABSTRACT

Compounds represented by the formula

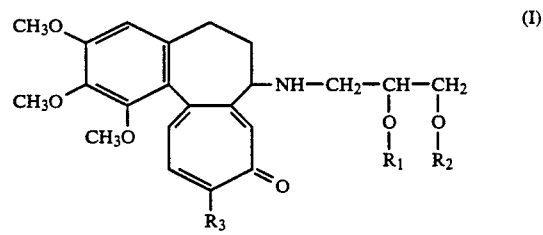

wherein
$R_1$ and $R_2$ each represent a hydrogen atom or a protective group for a hydroxyl group, or $R_1$ and $R_2$ combine to represent a protective group for hydroxyl groups, and
$R_3$ represents $CH_3O-$ or $CH_3NH-$.

These compounds exhibit a strong effect to inhibit proliferation of cancer cells and are expected to be used as a carcinostatic agent.

5 Claims, No Drawings

5,6,7,9-TETRAHYDRO-1,2,3-TRIMETHOXY-9-OXOBENZO[ALPHA]HEPTALENE DERIVATIVE AND PHARMACEUTICAL USE

This invention relates to novel 5,6,7,9-tetrahydro-1,2,3-trimethoxy-9-oxobenzo[α]heptalene derivatives, and more detailedly relates to compounds represented by the following formula and their salts, and a process for preparation thereof and their use as an antitumor agent:

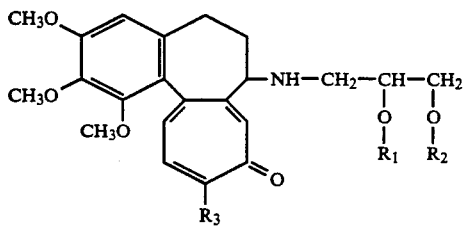

wherein
$R_1$ and $R_2$ each represent a hydrogen atom or a protective group for a hydroxyl group, or $R_1$ and $R_2$ combine to represent a protective group for hydroxyl groups, and
$R_3$ represents $CH_3O-$ or $CH_3NH-$.

It is already known that colchicine represented by the following formula

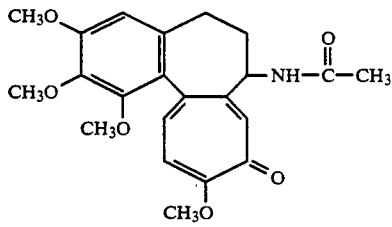

and N-methylcolchiceinamide represented by the following formula

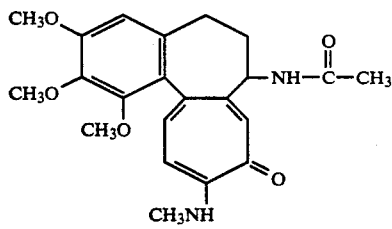

have pharmacologial actions on cancer cells, gout, etc. [Refer to E. E. van Tamelen, T. A. Spencer, Jr., D. S. Allen, Jr., and R. L. Orvis, Tetrahedron, 14 (8) (1961); and Journal of National Cancer Institute, 13, 731–739 (1952)].

However, the above colchicine and N-methylcolchiceinamide have strong toxicity, have no sufficient carcinostatic action, and, therefore, are not provided for actual pharmaceutical uses.

Thus, the present inventors intensely studied to find derivatives of colchicine or N-methylcolchiceinamide having a further excellent carcinostatic action, and as a result they have now found that the compounds represented by the above formula (I) and their salts exhibit a strong effect to inhibit proliferation of cancer cells and are expected to be used as a carcinostatic, and completed this invention.

As examples of the protective group for a hydroxyl group which each of $R_1$ and $R_2$ in the above formula (I) can represent, there can be mentioned $C_1$–$C_{10}$ (preferably $C_2$–$C_6$) alkanoyl groups such as acetyl, propionyl, butyryl and pivaloyl; and acyl groups such as aroyl groups, e.g. benzoyl. Further, as examples of the protective group for hydroxyl groups which $R_1$ and $R_2$ can combine to represent, there can be mentioned acetal or ketal groups represented by the formula

wherein
$R_4$ represents a hydrogen atom or a lower alkyl group; and
$R_5$ represents a lower alkyl group or a phenyl group, and more specifically

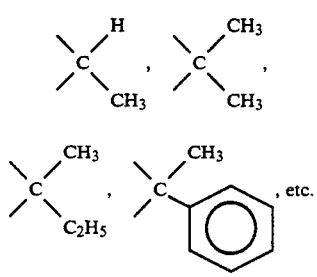

In the above, the word "lower" means that the carbon number of a group or compound to which this word is attached is 6 or less, preferably 4 or less.

Further, as salts of the compounds of the formula (I), there can, for example, be mentioned inorganic acid salts such as hydrochloride and sulfate; and organic acid salts such as acetate, propionate, butyrate, lactate, tartrate, malate, citrate, gluconate, succinate, maleate, fumarate, glytyllytinate, benzoate, etc.

A compound of the above formula (I) of this invention can, for example, be prepared by reacting a compound represented by the following formula

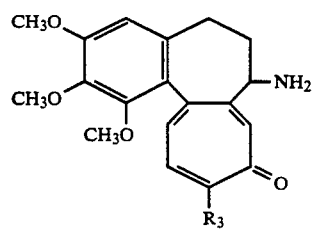

wherein $R_3$ has the above-mentioned meaning, with glyceraldehyde whose hydroxyl groups may appropriately be protected, represented by the following formula,

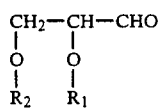 (III)

and reducing the resultant compound represented by the following formula

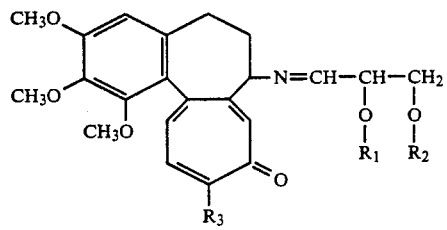 (IV)

wherein $R_1$, $R_2$ and $R_3$ have the same meanings as above.

The above reaction of a compound of the formula (II) with an aldehyde of the formula (III) is a reaction to form a Schiff's base, and can, for example, be carried out by contacting the compound of the formula (II) with the aldehyde of the formula (III) in a suitable solvent, for example, a halogenated hydrocarbon such as chloroform, dichloromethane or dichloroethane; an aliphatic ether such as ethyl ether or methyl cellosolve; an aromatic hydrocarbon such as benzene or toluene; or the like. In this occasion, it is extremely effective to use a dehydrating agent such as molecular sieves, anhydrous magnesium sulfate or anhydrous sodium sulfate. This reaction can be carried out usually at room temperature, but in some case can also be carried out at an elevated temperature up to above 40° C. The ratio of the aldehyde of the formula (III) to the compound of the formula (II) is not strictly limited, but generally, it is convenient to use the aldehyde in the range of 0.8 to 2.5 moles, particularly 0.9 to 1.5 moles per mole of the compound of the formula (II).

By this, a Schiff's base of the formula (IV) is obtained. A compound of the formula (I) of this invention can be obtained by reducing this Schiff's base. This reduction can be carried out either successively after formation of the Schiff's base of the formula (IV), or simultaneously with formation of the Schiff's base.

Thus, this reduction can, for example, be carried out by adding a reducing agent to the reaction system of the compound of the formula (II) and the aldehyde of the formula (III), or by treating the resultant Schiff's base of the formula (IV), in situ or after separation from the reaction mixture, with a reducing agent. As usable reducing agents, there can, for example, be mentioned metal hydride complexes such as sodium cyanoborohydride, sodium borohydride and tributyltin hydride. It is suitable to use such a reducing agent usually in the rate of 0.8 to 1.2 moles, particularly 0.9 to 1.1 moles per mole of the compound of the formula (II) as a starting raw material.

The above reduction can be carried out usually at a temperature between about −5° C. and about 20° C., preferably a temperature between about 0° C. and about 15° C.

By the above reduction is produced a compound represented by the following formula

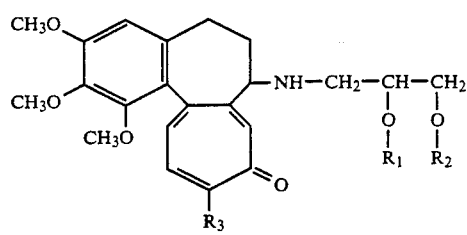 (I)

wherein $R_1$, $R_2$ and $R_3$ have the same meanings as above-mentioned.

Further, when one or both of $R_1$ and $R_2$ represents a protective group for a hydroxyl group, or $R_1$ and $R_2$ combine to represent a protective group for hydroxyl groups, there arises a case, according to the reduction conditions, where a compound represented by the following formula

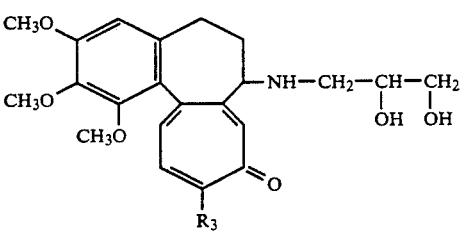 (I-1)

wherein $R_3$ has the same meaning as above-mentioned, is formed as a result of cleavage of the protective group, and further, when both $R_1$ and $R_2$ represent protective groups for hydroxyl groups, there also arises a case where a compound represented by the following formula

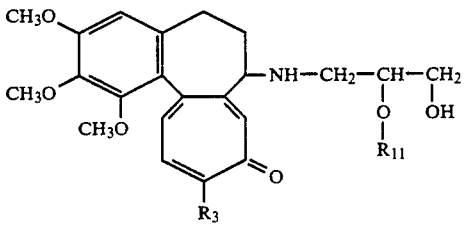 (I-2)

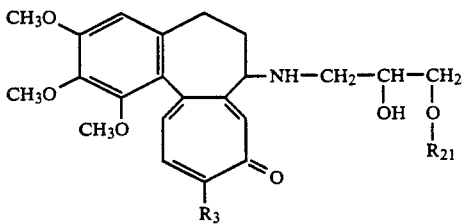 (I-3)

wherein
$R_{11}$ and $R_{21}$ each represent a protective group for a hydroxyl group, and
$R_3$ has the same meaning as above-mentioned, is formed as a result of partial cleavage thereof.

A compound of the formula (I) when $R_3$ is $CH_3NH-$, namely a compound represented by the following formula

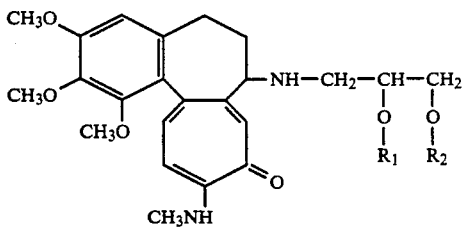

wherein $R_1$ and $R_2$ have the same meanings as above-mentioned, can also be prepared, for example, by methylaminating a compound of the formula (I) when $R_3$ represents $CH_3O$—, capable of being prepared according to the above-mentioned process, namely a compound represented by the following formula

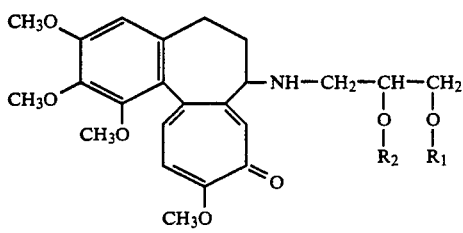

wherein $R_1$ and $R_2$ have the same meanings as above-mentioned.

The methylamination of a compound of the formula (I-5) can be carried out by a process known per se [for example, refer to Patrick J. Davis, Antimicrobial Agents and Chemotherapy, March 1981, P465–469; J. L. Hartwell et al., J. Am. Chem. Soc., 74, 3180 (1952)], for example by reacting the compound of the formula (I-5) with methylamine to substitute a methylamino group for the methoxy group at the 10-position.

The above reaction can be carried out generally at room temperature to the reflux temperature of the solvent, preferably at a temperature from about 40° to about 90° C. Further, although the ratio of methylamine to be reacted with a compound of the formula (I-5) is not strictly limited, it is convenient to use it usually in the range from about 2 to about 30 moles, particularly from about 10 to about 20 moles per mole of a compound of the formula (I-5).

The above methylamination reaction can, usually, be carried out in the presence of an aqueous medium in a closed vessel.

The thus obtained compound of the formula (I) of this invention can be separated and purified by methods known per se, for example, by extraction, chromatography, crystallization or a combination thereof, or the like.

A compound of this invention when $R_1$ and/or $R_2$ represent protective groups for hydroxyl groups can be subjected to a reaction for removal of the protective groups, for example hydrolysis to remove the protective groups.

Further, the thus obtained compound of the formula (I) can, if necessary, be converted to such a salt as above-mentioned, according to a reaction known per se to form a salt, for example, by treating it with a suitable acid.

A compound of the above formula (I) obtained by this invention contains an asymmetric carbon atom at the side chain, and can exist in the form of D-form, L-form or DL-form. For example, in the above preparation process, when a starting raw material of D-form is used as the glyceraldehyde of the formula (III), a compound of the formula (I) of D-form, can be obtained when a glyceraldehyde of the formula (III) of L-form is used, a compound of the formula (I) of L-form can be obtained, and when a glyceraldehyde of the formula (III) of DL-form is used, a compound of the formula (I) of DL-form can be obtained.

In the foregoing reactions, among the compounds of the formula (II), deacetylcolchicine, a compound of the formula (II) wherein $R_3$ represents $CH_3O$— is a compound known per se [refer to J. Am. Chem. Soc., 75, 5292 (1953)], and can be prepared according to a known process. Alternatively, deacetylcolchicine can also be prepared, according to the process newly developed by the present inventors (EP-A-493064), by reacting colchicine with triethyloxonium fluoroborate (Meerwein reagent) and then treating the product with water [as for the details, refer to the later-described Reference example 1].

On the other hand, N-methyldeacetylcolchiceinamide, a compound of the formula (II) wherein $R_3$ represents $CH_3NH$— can, for example, be prepared by reacting deacetylcolchicine with methylamine, or by reacting colchicine with methylamine to prepare N-methylcolchiceinamide [refer to J. L. Hartwell et al., J. Am. Chem. Soc., 74, 3180 (1952)] and then hydrolyzing (deacetylating) this in dilute sulfuric acid [as for the details, refer to the later-described Reference example 2].

As apparent from the following in vitro tests on cancer cells, the compounds of the above formula (I) provided by this invention exhibit an excellent carcinostatic action and only low toxicity.

TEST EXAMPLE 1

In Vitro Cancer Cell Proliferation Inhibiting Test (1) $10^6$ each of mouse leukemic cells p388/S and adriamycin-resistant mouse leukemic cells p388/ADR are suspended in RPMI 1640 media each containing 10% fetal bovine serum, respectively, and cultured for 2 days in the presence of a test compound (this was used after it was dissolved in dimethylsulfoxide to 1 mg/ml and the solution was diluted with a phosphate buffer). The influence of the test compound on cell proliferation was investigated, and 50% proliferation inhibitory concentration:$IC_{50}$ value (μg/ml) was determined. The results are shown in Table 1.

TABLE 1

| Test compound | $IC_{50}$ (μg/ml) | |
|---|---|---|
| | p388/S | P388/ADR |
| D—N-(O,O-isopropylideneglyceryl)-deacetylcolchicine | 0.014 | 0.038 |
| DL—N-(O,O-isopropylideneglyceryl)-deacetylcolchicine | 0.013 | 0.13 |
| L—N-(O,O-isopropylideneglyceryl)-deacetylcolchicine | 0.018 | 0.14 |
| Colchicine | 0.0041 | 0.48 |

(2) Mouse leukemic cells p388/S and adriamycin-resistant mouse leukemic cells P388/ADR subculturally transplanted in the abdominal cavity of mice were taken out together with the asites therefrom, respectively, and after washing, suspended in RPMI 1640 media (each containing 10% fetal bovine serum and 10 μM 2-mercaptoethanol) to $2 \times 10^5$ cells/ml, respectively.

Test solutions (solutions of the compound of the later-described Example 3 in phosphate-buffered physiological saline) were added to portions of each of these cell suspensions, respectively; and the mixtures were separately put into a 24-well culture plate and subjected to culture for 2 days in a 5% carbon dioxide culturing vessel. A 0.5% Trypan Blue solution was added to each of the cell culture broths in the same amount, and the 50% proliferation inhibitory concentration ($IC_{50}$) of the test compound was determined by counting the number of the cells not stained as living cells under a microscope. The results of the experiment carried out three times are shown in the following Table 2.

TABLE 2

| Test compound | $IC_{50}$ (ng/ml) | |
| --- | --- | --- |
| | p388/S | P388/ADR |
| Tartrate of | | |
| N-(O,O-isopropylidene- | 13.5 | 18.0 |
| glyceryl)-N-methyl- | 12.8 | 16.4 |
| deacetylcolchiceinamide | 14.9 | 19.2 |

TEST EXAMPLE 2

Acute Toxicity Test

Portions of test solutions (solutions of the compound of the later-described Example 3 in physiological saline) were intraperitoneally administered to groups of CDF male mice, each group consisting of 8 mice, respectively, and body weights, symptoms, dates of death, etc. were observed for 10 days. Application amounts reduced at a common ratio of 1.2 were settled with 432 mg/kg as a maximum amount, the $LD_{50}$ value thereof was calculated using the Litchfield Wilcoxon method, and as a result, the $LD_{50}$ of the compound of Example 3 was 269 mg/kg (233 to 310 mg/kg).

On acute toxicity symptoms, in the high administration groups, the lie of hair got worse on and after one day after administration, and cases where diarrhea or loss of hair arose were also observed. Further, as for weight change, body weight, in each case, tended to decrease up to 2 to 4 days after administration, but thereafter increased gradually.

As apparent from the above test results, the compounds of this invention have a strong inhibitory action on cancer cells, and only low toxicity, and are expected to be used as a carcinostatic.

When a compound of this invention is used as a drug such as a carcinostatic, the compound can be administered orally or parenterally (for example, injected intravenously, injected intramuscularly, injected subcutaneously, or the like). Its effective dose can be varied over a wide range depending on the symptom, the degree of the disease, the weight and the age of a patient to which the compound is to be administered, judgment of the doctor, etc., but, for example in case of injection, can, usually, be about 10 to about 50 mg/kg/day, and the compound can be administered once a day or in several divided doses a day.

When a compound of this invention is used as a drug, an effective amount of the compound can be formulated together with pharmaceutically acceptable carriers or diluents (for example, excipients, solvents, other auxiliaries, etc.) into administration unit forms suitable for administration, for example, dosage forms such as tablets, powders, granules, capsules, enteric agents, troches, syrups, elixirs, liquids, suspensions and emulsions.

As carriers or diluents usable for the above formulation, there can, for example, be mentioned excipients such as starch, lactose, sucrose, mannitol and carboxymethylcellulose; lubricants such as magnesium stearate, sodium lauryl sulfate and talc; binders such as dextrin, microcrystalline cellulose, polyvinylpyrrolidone, gum arabic, corn starch and gelatin; disintegrants such as potato starch and carboxymethylcellulose; diluents such as distilled water for injection, physiological saline, aqueous dextrose solutions, vegetable oils for injection, propylene glycol and polyethylene glycol; etc., and further if necessary, there can be compounded a flavor, a colorant, a tonicity agent, a stabilizer, an antiseptic, an agent to make a compound of this invention painless, etc.

Further, another pharmacologically active substance can, if necessary, be compounded in the drug of this invention.

This invention is more specifically described below according to examples.

REFERENCE EXAMPLE 1

Preparation of Deacetylcolchicine

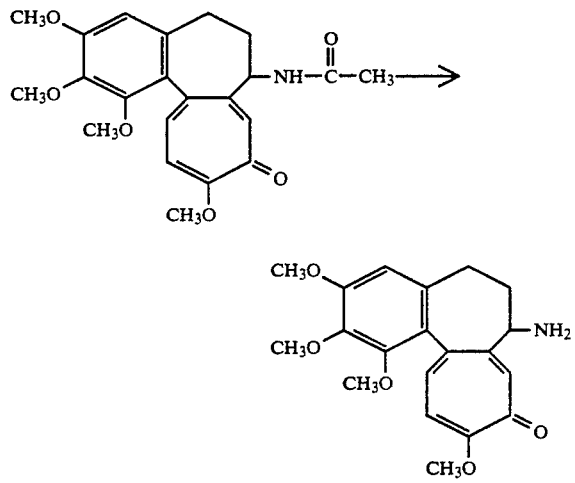

Colchicine (4.00 g, 10 mmoles) was dissolved in anhydrous methylene chloride, the solution was cooled to 0° C., and a methylene chloride solution (15 mmoles) triethyloxonium fluoroborate (Meerwein reagent) was added dropwise. The mixture was stirred at 0° C. for 1 hour and further at room temperature for 5 hours. 30 ml of water were added to the reaction mixture, and the resulting mixture was stirred for 1 hour. After the stirring, the aqueous layer was separated with a separating funnel. The methylene chloride layer was further extracted five times with 50 ml each of water. The methylene chloride layer was dried over magnesium sulfate and used to recover unreacted colchicine. The aqueous layer was adjusted to pH 10 with 1 N sodium hydroxide and extracted with chloroform. The chloroform layer was dried over magnesium sulfate and then concentrated in an evaporator. The residue was dissolved in 30 ml of ethanol, and 1 g of D-tartaric acid was added, followed by heating the mixture for 1 hour. After the mixture was cooled to room temperature, the formed precipitate was filtered. The obtained tartrate salt was dried in a desiccator (decomposed at a melting point of 219° to 220° C.).

The tartrate salt was dissolved in 50 ml of water, and the solution was readjusted to pH 10 with 1N sodium hydroxide, and extracted with chloroform. The extract was dried over magnesium sulfate and concentrated under reduced pressure in an evaporator to obtain 1.38 g of oily deacetylcolchicine. The yield was 39%.

Unreacted colchicine can be recovered from the eluate with a benzene-acetone solvent by silica gel column chromatography of the initial methylene chloride layer (1.71 g). The yield of deacetylcolchicine give by subtracting this is 61%.

REFERENCE EXAMPLE 2

Preparation of N-Methyldeacetylcolchiceinamide

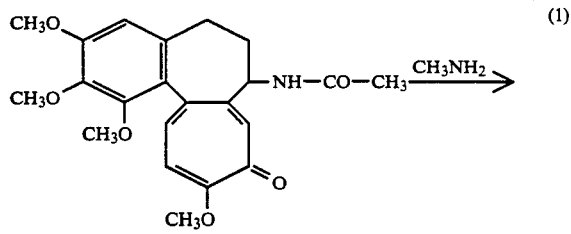

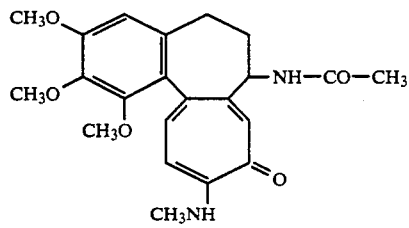

A mixed solution of colchicine (5.00 g, 12.5 mmoles), an aqueous 40% methylamine solution (10 ml, 130 mmol) and ethyl alcohol (10 ml) was subjected to reaction at 120° C. for 20 hours under stirring in a sealed tube. The solvent was distilled off, water (10 ml) was added to the residue, and the mixture was extracted with chloroform. The chloroform layer was separated, washed with water and dried. The solvent was evaporated, and the residue was separated and purified by silica gel column chromatography [chloroform:methanol (20:1)]. Thereby, 4.18 g of N-methylcolchiceinamide was obtained as yellow crystals (yield 84%).

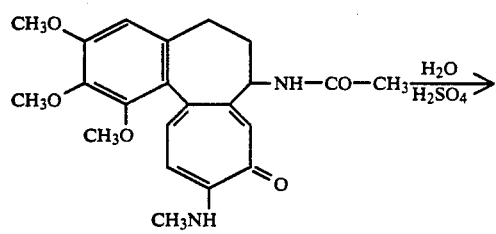

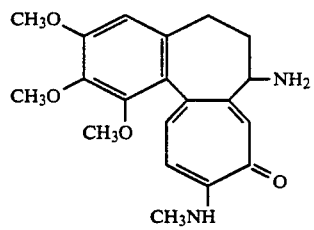

A mixed solution of N-methylcolchiceinamide (3.00 g, 7.5 mmoles), water (50 m) and concentrated sulfuric acid (15 ml) was stirred at 100° C. for 5 hours to make hydrolysis (deacetylation reaction). The reaction solution was made alkaline with anhydrous sodium carbonate under ice cooling, and extracted with chloroform. The chloroform layer was separated, washed with water and dried. The solvent was evaporated to dryness. The residue was subjected to separation and purification by silica gel column chromatography [chloroform:methanol (20:1)]. Thereby, 2.20 g of N-methyldeacetylcolchiceinamide was obtained as yellow crystals (yield 62%).

EXAMPLE 1

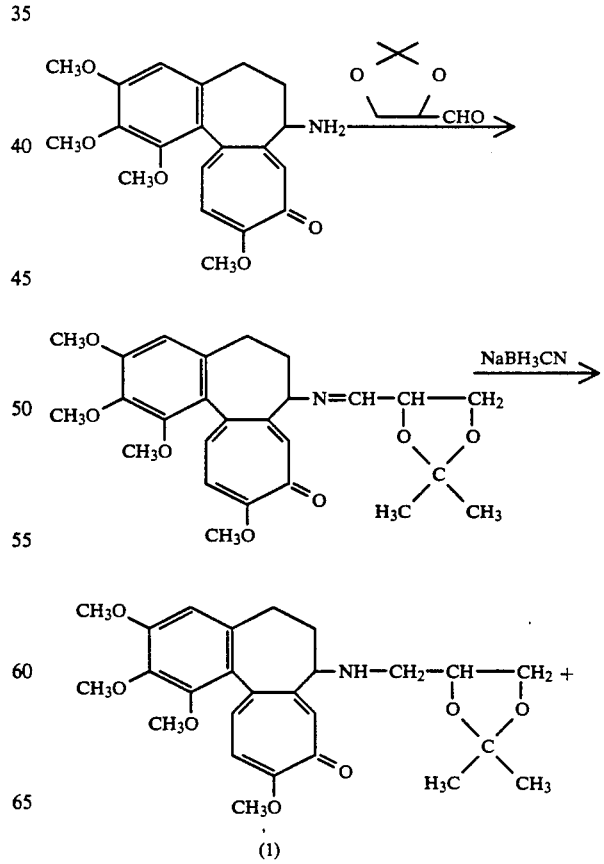

-continued

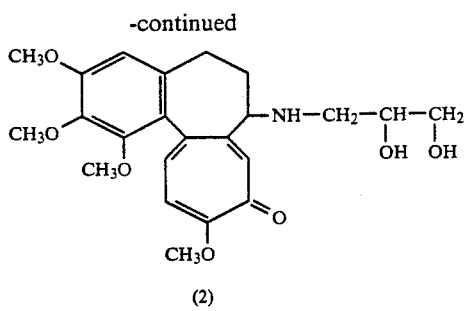

(2)

Deacetylcolchicine tartrate salt (4.06 g, 8.0 mmoles) was suspended in water (50 ml), and the suspension was made to pH of about 10 with 1N NaOH. The mixture was extracted with chloroform, the extract was dried over magnesium sulfate, the solvent was removed, and the residue was used as deacetylcolchicine. DL-O,O-isopropylideneglyceraldehyde (1.04 g, 8 mmoles) and magnesium sulfate (1.50 g) were added to a solution of this deacetylcolchicine in dry chloroform (30 ml), and the mixture was stirred at room temperature for 3 hours. After completion of the reaction, magnesium sulfate was removed by filtration, and the filtrate was concentrated in an evaporator. Dry methanol (20 ml ) was added to the residue to dissolve it, NaBH₃CN (0.76 g, 8.0 mmoles) was added under ice cooling, and the mixture was stirred at 0° C. for 1 hour and then at room temperature for 10 hours. During the stirring, the brown reaction mixture was turned gradually into yellow. After completion of the reaction, the reaction mixture was poured into 100 ml of water, and the mixture was extracted with chloroform. The chloroform layer was washed with saturated saline and dried over magnesium sulfate. The chloroform was distilled off under reduced pressure, and the residue was subjected to separation by silica gel column chromatography to obtain 1.85 g (49%) of DL-N-(O,O-isopropylideneglyceryl)deacetylcolchicine (1) from the benzene-acetone (6:1) eluate.

Amorphous solid

IR: 1260, 1140, 1100 cm$^{-1}$ (—O—) NMR: $\delta = 1.28$ (3H,s), 1.33 (3H,s), 2.22–2.73 (4H,m), 3.29–3.56 (2H,m), 3.58 (3H,s), 3.87 (3H,s), 3.89 (3H,s), 3.96 (3H,s), 3.67–4.18 (3H,m), 6.53 (1H,s), 6.84 (1H,s), 7.16 (1H,d), 7.80 (1H,s)

Further, 1.63 g (47%) of DL-N-(glyceryl)deacetylcolchicine (2) was also obtained from the same eluate.

Amorphous solid

IR: 3450 cm$^{-1}$ (OH), 1260, 1140, 1100 cm$^{-1}$ (—O—) NMR: $\delta = 1.98$–2.89 (8H,m), 3.60 (3H,s), 3.87 (3H,s), 3.89 (3H,s), 3.93 (3H,s) 3.53–4.00 (3H,m), 6.51 (1H,s), 6.53 (1H,s), 7.18 (1H,s), 7.31 (1H,s)

EXAMPLE 2

The same reaction as in Example 1 was carried out using D-O,O-isopropylideneglyceraldehyde ( 1.04 g, 8.0 mmoles) as a starting raw material to obtain 0.87 g (23%) of D-N-(O,O-isopropylideneglyceryl)deacetylcolchicine and 1.25 g (36%) of D-N-(glyceryl)deacetylcolchicine.

Its IR and NMR were almost the same with those of the compound of DL-form.

EXAMPLE 3

The same reaction as in Example 1 was carried out using L-O,O-isopropylideneglyceraldehyde (1.04 g 8.0 mmoles) as a starting raw material to obtain 0.84 g (22%) of L-N-(O,O-isopropylideneglycerol)deacetylcolchicine.

Its IR and NMR were almost the same with those of the compound of DL-form. In NMR, the position of absorption due to methyl of the isopropylidene group was slightly different, and absorption was observed at 1.29 ppm and 1.31 ppm.

EXAMPLE 4

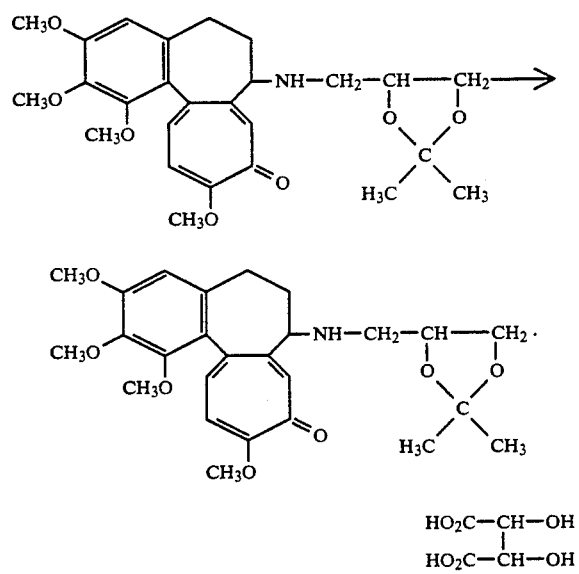

3.40 g (7.2 mmoles) of DL-N-(O,O-isopropylideneglyceryl)deacetylcolchicine obtained in Example 1 was dissolved in 50 ml of ethanol, 1.08 g (7.2 mmoles) of D-tartaric acid was added to the solution, and the mixture was warmed at 50° to 60° C. for 30 minutes. Thereafter, ethanol was distilled off under reduced pressure until the volume of the mixture became about ¼, and diethyl ether was added to the residual ethanol solution under ice cooling to precipitate crystals. The crystals were suction filtered and dried under reduced pressure to obtain DL-N-(O,O-isopropylideneglyceryl)deacetylcolchicine D-tartrate salt as yellow crystals. Melting point 96°–98° C. Yield 3.20 g (72%).

$^1$H-NMR (60 MHz) CDCl₃, $\delta$:1.02, 103 (each 3H, each s), 1.43–2.92 (5H,m), 3.40–4.40 (5H,m), 3.68 (3H,s), 4.00 (6H,s), 4.36 (3H,s), 6.86 (1H,s), 7.30 (1H,s), 7.40, 7.49 (each 1H,d,J = 11Hz)

EXAMPLE 5

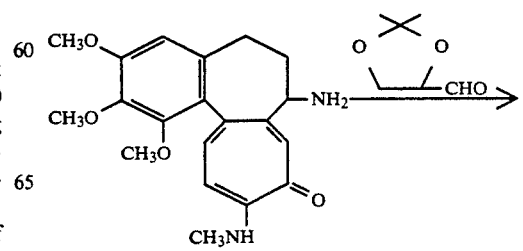

-continued

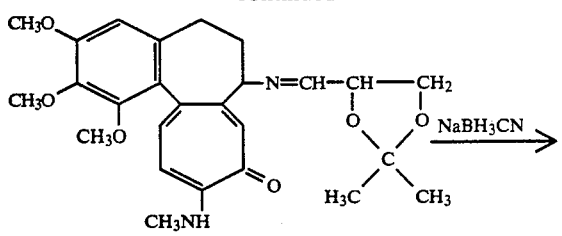

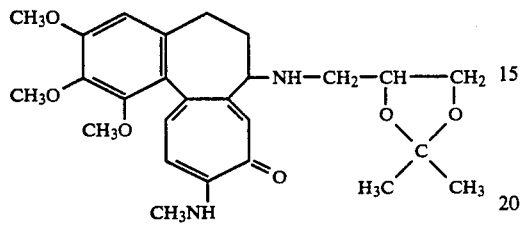

A benzene (20 ml) solution of O,O-isopropylideneglyceraldehyde (0.73 g, 5.6 mmoles) was added to a chloroform (30 ml) solution of N-methyldeacetylcolchiceinamide (2.00 g, 5.6 mmoles) in a flask, a Soxhlet extractor in which molecular sieves were put was set, and the mixture was refluxed for 5 hours. After completion of the reaction, the mixture was concentrated in an evaporator, and dry methanol (30 ml) was added to the residue to dissolve it. The solution was cooled to 0° C., and sodium cyanoborohydride (0.43 g, 5.6 mmoles) was added portionwise. The reaction mixture was stirred at 0° C. for 1 hour and then at room temperature for 10 hours. The reaction mixture was poured in 150 ml of water, the resultant mixture was extracted with chloroform, and the chloroform layer was washed with saturated saline and dried over magnesium sulfate. The chloroform layer was concentrated under reduced pressure and subjected to separation by silica gel column chromatography. 0.70 g (yield 27%) of N'-(O,O-isopropylideneglyceryl)-N-methyldeacetylcolchiceinamide was obtained from the benzeneacetone (3:1) eluate.

IR: 3500 cm$^{-1}$ (NH) NMR: δ = 1.30, 1.32 (3H,s), 1.35, 1.39 (3H,s), 2.25–2.50 (2H,m), 3.09 (3H,d,J = 5.4Hz), 3.59 (3H,s), 3.76–3.82 (1H,m), 3.90 (3H,s), 3.93 (3H,s), 3.89–4.03 (2H,m), 6.54 (1H,s), 7.27 (1H,s), 7.64 (1H,s), 7.77 (1H,s)

EXAMPLE 6

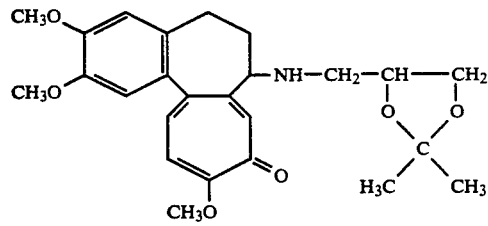

N-(O,O-isopropylideneglyceryl)deacetylcolchicine (2.74 g, 5.8 mmoles) obtained in the same manner as described in Example 1 and 10 ml of an aqueous 40% methylamine solution were put in a sealed tube, and stirred with heating to 75° to 80° C. for 20 hours. After completion of the reaction, the reaction mixture was concentrated in an evaporator, and the residue was dissolved in chloroform. The chloroform layer was washed with saturated saline and dried over magnesium sulfate. Chloroform was distilled off under reduced pressure, and the residue was subjected to separation and purification by silica gel column chromatography. As a result, 1.91 g (yield 70%) of N'-(O,O-isopropylideneglyceryl)-N-methyldeacetylcolchiceinamide identical to that in Example 5 was obtained from the benzene-acetone (3:1) eluate.

EXAMPLE 7

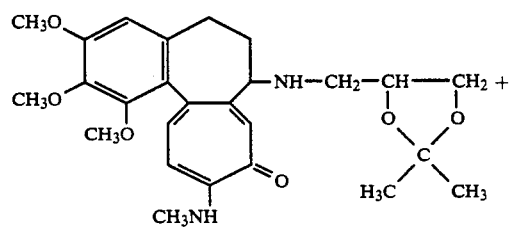

D-tartaric acid (1.08 g, 7.2 mmoles) was added to an ethanol (50 ml) solution of N-[(O,O-isopropylidene)-glyceryl]-N-methyldeacetylcolchiceinamide (3.40 g, 7.2 mmoles) obtained in Example 5, and the mixture was warmed at 50° to 60° C. for 30 minutes. Part of the ethanol was distilled off (until the volume became about ½), and diethyl ether was added to the residual ethanol solution under ice cooling to precipitate crystals. These crystals were suction filtered and dried under reduced pressure to obtain 3.30 g (yield 74%) of N'-(O,O-isopropylideneglyceryl)-N-methyldeacetylcolchiceinamide tartrate salt.

EXAMPLE A

Preparation of an Injection 30 g of N'-(O,O-isopropylideneglyceryl)-N-methyl-deacetylcolchiceinamide tartrate salt was dissolved in 1 L of distilled water for injection, the solution was made isotonic with sodium chloride, and the mixture was put into ampoules which were then sealed. 1 ml of this injection contains 30 mg of the effective ingredient.

I claim:

1. A compound represented by the following formula and a salt thereof:

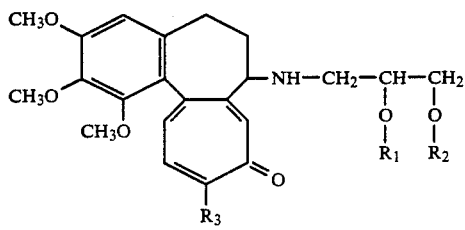

wherein $R_1$ and $R_2$ each represent a hydrogen atom or a protective group for a hydroxyl group, or $R_1$ and $R_2$ combine to represent a protective group for hydroxyl groups, and $R_3$ represents $CH_3O-$ or $CH_3NH-$.

2. The compound according to claim 1 wherein $R_1$ and $R_2$ each represent a hydrogen atom, a $C_1-C_{10}$ alkanoyl group or an aroyl group, or $R_1$ and $R_2$ combine to represent an acetal or ketal group denoted by the formula

wherein $R_4$ represents a hydrogen atom or a $C_1-C_6$ alkyl group and $R_5$ represents a $C_1-C_6$ alkyl or a phenyl group.

3. The compound according to claim 1 selected from N-(O,O-isopropylideneglyceryl)deacetylcolchicine and N'-(O,O-isopropylideneglyceryl)-N-methyldeacetylcolchiceinamide.

4. A pharmaceutical preparation comprising an effective amount of a compound of the formula (I) set forth in claim 1 or a pharmaceutically acceptable salt thereof, and pharmaceutically acceptable carrier(s) or diluent(s).

5. A method for treatment of leukemia which comprises administering a leukemic effective amount of a compound of the formula (I) set forth in claim 1 or a pharmaceutically acceptable salt thereof.

* * * * *